United States Patent
Choi et al.

(10) Patent No.: US 8,299,304 B2
(45) Date of Patent: Oct. 30, 2012

(54) ALIGNMENT MATERIAL FOR LIQUID CRYSTAL DISPLAY DEVICE OF VERTICAL ALIGNMENT MODE AND METHOD OF PREPARING THE SAME

(75) Inventors: Jin wook Choi, Hwaseong (KR); Dal bong Seo, Hwaseong (KR); Jae cheol Park, Hwaseong (KR); Yong bae Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 943 days.

(21) Appl. No.: 12/281,326

(22) PCT Filed: Feb. 9, 2007

(86) PCT No.: PCT/KR2007/000702
§ 371 (c)(1),
(2), (4) Date: Sep. 1, 2008

(87) PCT Pub. No.: WO2007/097535
PCT Pub. Date: Aug. 30, 2007

(65) Prior Publication Data
US 2011/0105698 A1    May 5, 2011

(30) Foreign Application Priority Data

Feb. 22, 2006  (KR) .................. 10-2006-0017148

(51) Int. Cl.
C07C 209/00 (2006.01)
C07C 291/00 (2006.01)
C07C 211/00 (2006.01)

(52) U.S. Cl. ........ 564/297; 525/436; 564/298; 564/299; 564/305; 564/306

(58) Field of Classification Search .................. 564/297, 564/298, 299, 305, 306; 525/436
See application file for complete search history.

(56) References Cited

U.S. PATENT DOCUMENTS
6,111,059 A * 8/2000 Nihira et al. .................. 528/353
* cited by examiner

*Primary Examiner* — Ana Woodward
(74) *Attorney, Agent, or Firm* — Lexyoume IP Meister, PLLC.

(57) ABSTRACT

This invention provides alignment materials for liquid crystal display device of vertical alignment mode and methods for the preparation of the same, and more particularly, it provides diaminobenzene derivatives represented by the following formula 1 (shown in description), capable of aligning liquid crystal in uniform and vertical way and remarkably improving clarity and solubility against organic solvents, methods for the preparation of the same and liquid crystal alignment films using the same.

1 Claim, No Drawings

ALIGNMENT MATERIAL FOR LIQUID CRYSTAL DISPLAY DEVICE OF VERTICAL ALIGNMENT MODE AND METHOD OF PREPARING THE SAME

TECHNICAL FIELD

This invention relates to alignment materials for liquid crystal display device of vertical alignment (hereafter, VA) mode and methods for the preparation of the same, and more particularly, to diaminobenzene derivatives represented by formula 1 as shown below capable of aligning liquid crystal in uniform and vertical way and remarkably improving clarity and solubility against organic solvents, methods for the preparation of the same and liquid crystal alignment films using the same.

BACKGROUND ART

Several liquid crystal driving modes have been proposed and developed to improve its display performance. The control of certain pretilt angles according to the driving modes is needed, and an alignment film that generates pretilt angles in a stable way becomes an essential element in determining the performance of LCD. Basically, alignment films align liquid crystal molecules, and they form pretilt angles between substrate planes and liquid crystal molecules so that they make reactivity good and ensure the alignment stability of liquid crystal molecules. Also, the alignment film is an important factor in determining credibility, display uniformity, after-image and voltage-holding ratio, etc. in liquid crystal display devices.

Numerous materials ranging from inorganic materials to organic polymers have been applied as materials for alignment films. Of them, the mostly-used representative polymer compounds are soluble polyimide based polymer compositions and polyamide acid based polymer compositions using polyamide acids through imidization. They are widely used as alignment materials that align liquid crystal in industrial fields by virtue of their excellent heat resistance and chemistry resistance. These polymer compounds are formed by the polymerization of diamine and tetracarboxylic acid dianhydrides, where the structure of monomers determines the properties of polymer compounds synthesized therefrom.

In general, as means for obtaining high pretilt angles, side-chained polyimide compounds have been used. Side chain structure can be introduced into either diamine or tetracarboxylic acid dianhydride but in most cases, diamine is used because side chain groups can be easily introduced thereinto. In general, there have been known polyimide liquid crystal alignment materials using as a monomer, an aliphatic, side-chained diamine having a straight alkoxy group, alkyl ester group or fluorinated alkyl group as a side chain. However, as the distribution and length of the side chains are not controlled in such polyimide alignment films, their pretilt angles were often as low as 3~25 degree or so.

In the side-chained polyimides, the several characteristics of the alignment films are determined according to aromatic and aliphatic components. Since the aromatic components act as a rigid core in polymer chains, they result in low solubility in organic solvents and thus decrease processability in industry. In addition, as they make the formation of charge transfer complex between polymer chains easy, they cause low permeability in the visible ray region. In particular, in TFT-type liquid crystal display devices, voltage holding ratio acts as an important factor in display characteristics of liquid crystal display devices and alignment films containing aromatic components in large amounts readily absorb ions so that they decrease applied voltage, resulting in decrease in contrast.

On the contrary, alignment films containing aliphatic or alicyclic classes in large amounts can improve the above-mentioned drawbacks. However, aliphatic polyamide acid based alignment materials have poor alignment properties of liquid crystal and aliphatic soluble polyimides have reduced adhesion to substrates so that even weak rubbing can readily chip off coating membranes. Although there are alignment materials where polyimides and polyamic acids are blended to complement such drawbacks, they have problems that the two materials are separated by heat and in particular, liquid crystal alignment materials prepared by the block copolymerization of the polyimides and polyamic acids involve too complicated preparation routes.

DISCLOSURE OF INVENTION

Technical Problem

In order to solve the problems of the prior arts, it is an object of the invention to provide a diaminobenzene derivative which is an alignment material for liquid crystal display device of vertical alignment mode, capable of aligning liquid crystal in uniform and vertical way and remarkably improving clarity and solubility against organic solvents, a method for the preparation of the same and a liquid crystal alignment film using the same.

Technical Solution

To achieve the aforementioned objects, the present invention provides a di-aminobenzene derivative represented by formula 1:

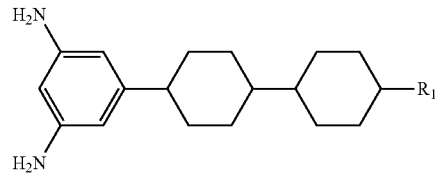

wherein $R_1$ is an alkyl group or alkoxy group of 5 to 7 carbon atoms.

Further, the invention provides a method for the preparation of the diamine compound represented by formula 1 as defined above comprising:

a) preparing a compound of formula 2:

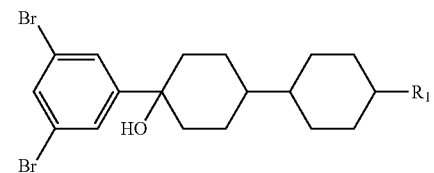

wherein $R_1$ is an alkyl or alkoxy group of 5 to 7 carbon atoms by reacting 4-alkylbicyclo-4-one compound with 1,3,5-tribromobenzene;

b) preparing a compound of formula 3:

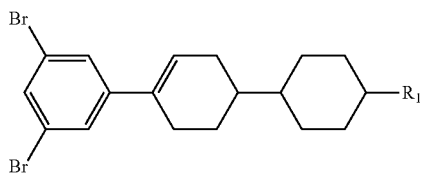

wherein $R_1$ is an alkyl or alkoxy group of 5 to 7 carbon atoms by hydrating the compound of formula 2 under para-toluenesulfonic acid 1-hydrate;

c) preparing a compound of formula 4:

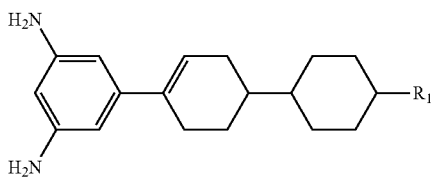

wherein $R_1$ is an alkyl or alkoxy group of 5 to 7 carbon atoms by reacting the compound of formula 3 with lithium bis(trimethylsilyl)amide, (dibenzylideneacetone)palladium, and tricyclohexylphosphine; and d) hydrogen reducing the compound of formula 4 under a Pd/C catalyst and separating a trans isomer compound therefrom.

Still further, the invention provides a method for the preparation of a polyimide resin for vertical alignment material of liquid crystal display device comprising:

a) preparing a polyamic acid based block copolymer by reacting a side-chained diamine compound of formula 1 as defined above, a tetracarboxylic acid anhydride of formula 5:

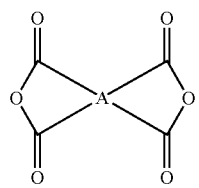

wherein A is a tetravalent organic group, and a diamine compound having no side chain group of formula 6:

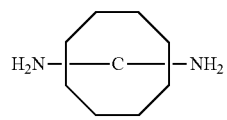

wherein C is a bivalent organic group having no side chains, under a solvent; and b) converting the polyamic acid based block copolymer into a polyimide through ring-closing dehydration by thermal treatment.

Still further, the invention provides a liquid crystal alignment film prepared by using the polyimide resin as described above.

Still further, the invention provides a liquid crystal display device comprising the above liquid crystal alignment film.

Advantageous Effects

The side-chained diamine compounds of formula 1 of the present invention are useful for the manufacturing of polyimide resins for non-rubbing vertical alignment materials, and the polyimide resins prepared using the diamine compounds have good vertical alignment of liquid crystal and can exert pretilt angles of 89 degree or more with non-rubbing methods regardless of rubbing process conditions and furthermore, the polyimide resins in accordance with the invention have remarkably improved clarity and solubility against organic solvents and thus they are useful as alignment material for liquid crystal display device.

MODE FOR THE INVENTION

This invention is further described in detail

The liquid crystal alignment materials according to the invention are characterized in that they have an alkyl chain group, and alicyclic side chain as shown in above formula 1 by being designed to have the side chain so that they can align liquid crystal in uniform and vertical way and remarkably improve clarity and solubility against organic solvents.

In the above formula 1, the side chain has been designed to achieve the objects of the invention. The alkyl chain located on the terminal of the side chain lowers surface tension so as to exert vertical alignment properties and creates spaces into which organic solvents can penetrate between polymer chains, thereby increasing solubility. The polyimides themselves that merely have the alkyl chain as a side chain fail to exhibit vertical alignment properties.

Also, the aliphatic rings hold liquid crystal molecules vertically and further, their rigid core groups and terminal alkyl group are linked in such a bar shape as liquid crystal and thus can increase vertical alignment properties by the interaction with the lateral sides of the liquid crystal when the liquid crystal was placed around the side chain. Also, the polyimide resins having the side chains determine the length of diamine side chains and the length between the side chains, depending on the average length of the long axis of the liquid crystal molecules and the size of required pretilt angles. The present invention controls these elements and it is thus possible to control the characteristics of polyimide based copolymers.

The bicyclohexyl group linked to the terminal alkyl chain inhibits the formation of charge transfer complex within the polyimides better than those containing phenyl groups do, it allows more liberal movement than the stiff structures of biphenyl groups and thus contributes the improvement of solubility along with the terminal alkyl chain, and it shuts off the absorption of visible ray by decrease in the formation of charge transfer complex when alignment films are formed, thereby ensuring clarity. Also, it decreases ion adsorption onto the surface of alignment films when electric field is applied in TFT-type liquid crystal display devices and thus can improve voltage holding ratio.

Also, the side chain containing polyimide resins determine the length of diamine side chains and the length between the side chains, depending on the average length of the long axis of the liquid crystal molecules and the size of required pretilt angles. Preferably, the length of the side chain group in the side-chained diamine compounds of formula 1 above is determined such that the ratio of the length of the polyimide side chain group and the average length of the long axis of the liquid crystal molecules is within the range of 0.8 to 1.5. The width between the side chain groups is an important factor in determining the density of side chain groups arranging on substrate surface. Therefore, it is preferable to insert diamine compounds having no side chains into the main chain of the polyimides such that the length between the polyimide side chain groups becomes 1.5 to 3.5 times the length of the liquid crystal molecules.

The side-chained diamine compounds of formula 1 above can be prepared via such methods as reaction flow 1:

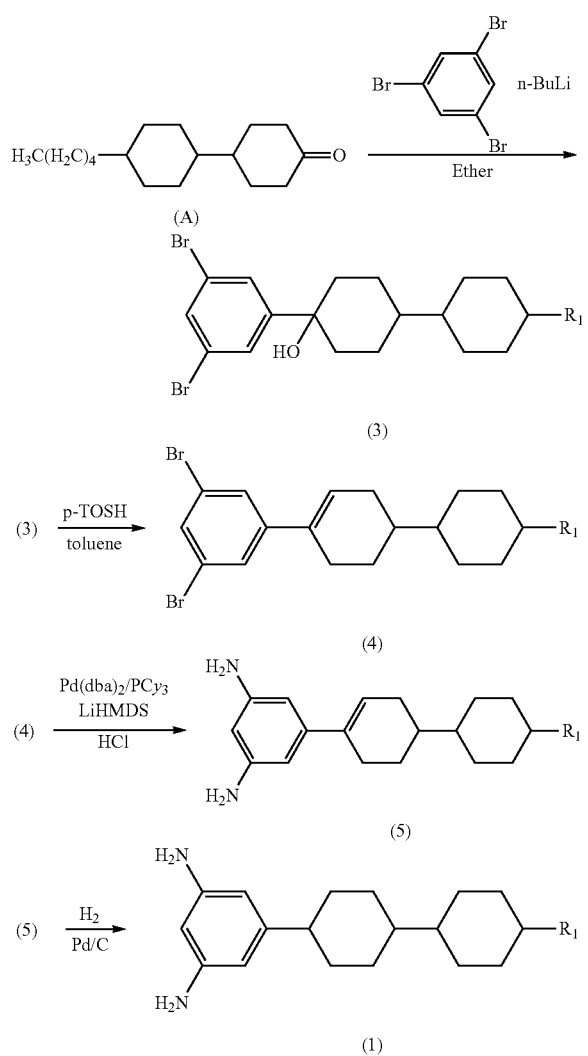

wherein $R_1$ is an alkyl or alkoxy group of 5 to 7 carbon atoms.

Step 1

Under nitrogen atmosphere, π-BuLi is dropwise added to a solution prepared by dissolving 1,3,5-tribromobenzene in ether while the temperature is being kept not to exceed −78° C., and 4-alkylbicyclohexyl-4-one (A) is added to the thus prepared reaction solution and stirred, whereby 4-(3,5-dibromophenyl)-4-alkylbicyclohexyl-4-ol compound of formula 2 can be obtained. The amount of the compound (A) and 1,3,5-tribromobenzene is used in equivalent ratio.

Step 2

4-(3,5-dibromophenyl)-4-alkylbicyclohexyl-3-ene of formula 3 can be obtained by hydrating the compound of formula 2 above under paratoluenesulfonic acid, 1-hydrate.

Step 3

The diamine compound of formula 4, 5-(4-alkylbicyclohexyl-3-ene-4-yl)-benzene-1,3-diamine can be obtained by reacting the compound of formula 3 above with lithium bis (trimethylsilyl)amide, (dibenzylideneacetone)palladium, and tricyclohexylphosphine.

Step 4

The final diamine compound of formula 1, 5-(trans-4-alkylbicyclohexyl-3-ene-4-yl)-benzene-1,3-diamine compound can be obtained by hydrogen reducing the compound of formula 4 above under a Pd/C catalyst and separating isomers.

Further, the present invention provides a method for the preparation of polyimide resins using the diamine compound of formula 1 above and the polyimide resins, and the method for the preparation of the polyimide resins is characterized by comprising a) preparing a polyamic acid based block copolymer by reacting a side-chained diamine compound of formula 1 as defined above, a tetracarboxylic acid anhydride of formula 5:

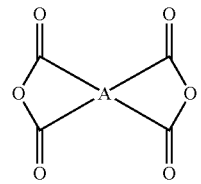

wherein A is a tetravalent organic group, and a diamine compound having no side chain group of formula 6:

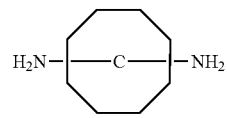

wherein C is a bivalent organic group having no side chains, under a solvent; and b) converting the polyamic acid based block copolymer into a polyimide through ring-closing dehydration by thermal treatment.

As a specific example, tetracarboxylic acid dianhydride of formula 5 above is slowly dropwise added to a reaction solution of the side-chained diamine compound of formula 1 above and the diamine of formula 6 above dissolved in N-methyl-2-pyrrolidone under nitrogen atmosphere for 2 hours while the temperature is being kept at 5° C., and stirred for 6 hours to prepare polyamic acid based block copolymers. The viscosity can be adjusted by using such cellosolve type solvents as diethyleneglycolmonomethylether, diethyleneglycolmonoethylether, ethyleneglycolmonobutylether, etc.

Then, the polyamic acid based block copolymers can be converted into polyimides having a repeat unit of formula 5 through ring-closing dehydration reaction by thermal treatment between 100 to 230° C. for 30 min to 2 hours.

As the solvents, it is preferable to use inert solvents. Specific examples of the inert solvents are N-methyl-2-pyrrolidone (NMP), N,N-dimethylformamide (DMF), dimethylsulfoxide (DMSO), hexamethylphosphoramide, tetramethylenesulfone, p-chlorophenol, p-bromophenol, 2-chloro-4-hydroxytoluene, dioxane, tetrahydrofuran (THF), cyclohexanone and the like.

As tetracarboxylic acid dianhydride of formula 5 above, compounds having a tetravalent organic group can be employed. Their specific examples are 3,3',4,4'-benzophenonetetracarboxylic acid dianhydride, 4,4'-oxydiphthalic anhydride (ODPA), 3,3',4,4'-biphenyltetracarboxylic acid dianhydride (BPDA), 1,2,4,5-benzenetetracarboxylic acid dianhydride (PMDA), cis-1,2,3,4-cyclopentanetetracarboxylic acid dianhydride (CPDA), cyclobutanetetracarboxylic acid dianhydride (CBDA) and 4-(2,5-dioxotetrahydrofuran-3-yl)-1,2,3,4-tetrahydronaphthalene-1,2-carboxylic acid dianhydride (TDA).

Also, as the diamine compounds of formula 6 above, diamine compounds having no lateral substituents can be used. Specifically, there are 4,4'-diaminodiphenylether (ODA), 4,4'-methylenebiscyclohexylamine (PACM), 4,4'-methylene-2-methylcyclohexylamine (ANCAMINE), 4,4'-methylenedianiline, diaminobenzophenone, 4,4'-methylenediphenyldiamine (MDA), 4,4'-hexafluoroisopropyldiphenyldiamine (6FDA), p-phenylenediamine, etc.

The compound included in formula 1 which is the side-chained bivalent organic group in the polyimides is used to confer improvement in response rate properties and vertical alignment properties and the bivalent organic group (C) having no side chains is used to control the width between the side chains and determine the distribution of the side chain groups.

The side chain length of the side-chained bivalent organic group is controlled to be 0.8 to 1.5 times the average length of the long axis of the liquid crystal molecules. Also, it is advisable to determine the type and amount of the bivalent organic group (C) such that the length between the side chains can be 1.5 to 3.5 times the length of the long axis of the liquid crystal molecules. More preferably, the compound of formula 5 in the above is used in the same mole amount as the total moles of the compound of formula 1 and the compound of formula 6 above, and the amount of the compound of formula 1 and the compound of formula 6 is preferably 1:1 to 10 in molar ratio, more preferably 2 to 4. The above method enables the preparation of the polyimide resins having a specific structure, of which the side chains can show excellent vertical alignment properties and improved properties in solubility and membrane permeability. Preferably, the average weight molecular weight of the polyimide resins is 1,000 to 200,000.

Further, the present invention provides liquid crystal alignment films using the polyimide resins, and the liquid crystal alignment films can be obtained by coating the alignment solutions comprising the polyimide compounds onto patterned substrates and then calcining them. The solvents used in the alignment solution are usually used in the liquid crystal alignment solutions and they are not limited to specific ones as long as they can dissolve the polyimide compounds, and the alignment solutions preferably include the polyimide compounds in an amount of 1 to 30% by weight.

Also, the alignment solution can be used by being further blended with di-aminosiloxane represented by formula 9:

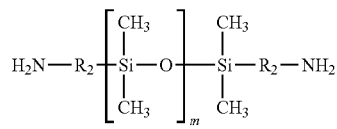

wherein $R_2$ is a bivalent organic group aliphatic or aromatic hydrocarbon group having 3 to 6 carbon atoms, and m is an integer of 1 to 100, in order to increase adhesion to substrate surface. Preferably, the diaminosiloxane is included in an amount of 0.1 to 20% by weight.

The liquid crystal alignment films of the present invention align the liquid crystal in uniform and vertical way and have high pretilt angles and in particular, they can remarkably improve solubility against a variety of solvents and clarity of alignment films The present invention will be described in detail by reference to the following examples, by which the invention is not limited in any way.

EXAMPLES

Example 1

The diamine compounds of formula 1 were synthesized by reaction flow 1. Synthesis in each step is as follows.

(Step 1)

63.0 g (0.2 mol) of 1,3,5-tribromobenzene was dissolved and added to 1400 ml of ether and nitrogen atmosphere was kept. The solution was slowly dropwise added to 80 ml (0.2 mol) of 2.5 M normal butyl lithium (n-BuLi) while the temperature was being kept at −78° C. After the reaction solution was kept for one and half hours below −78° C., 50 g (0.2 mmol) of 4'-pentylbicyclohexyl-4-one dissolved in 50 ml of ether was slowly dropwise added thereto. After the completion of the dropwise addition, the temperature was still kept for 30 min below −78° C. Then, it was allowed to reach room temperature and then the reaction mixture was poured into 1 L of distilled water and the organic layer was separated. The water layer was extracted with ether and the organic layer was washed with a saturated NaCl aqueous solution and then, residual moisture was dried over $MgSO_4$. The solvent was distilled under a reduced pressure, affording 82 g (0.149 mol) of a yellow solid with a yield of 84%.

Mass: 486(M+), 468, 439, 315, 301, 291, 278, 263, 249, 235, 219, 206, 193, 171, 151, 139, 128, 111, 97, 81, 69, 55

(Step 2)

70 g (0.14 mol) of 4-(3,5-dibromo-phenyl)-4'-pentyl-bicyclohexyl-4-ol and 2.7 g (0.014 mol) of p-toluenesulfonic acid, 1-hydrate were added, followed by the addition of 600 ml of toluene. The solution was reacted with reflux for 12 hours. After the completion of the reaction, which was checked by TLC plate, it was washed with a saturated NaCl aqueous solution and ether and extracted. The residual moisture was dried over $MgSO_4$ and distilled under a reduced pressure, providing brown oil. It was chromatographied with hexane as a development solution, affording 61 g (0.13 mol) of a pure colorless liquid with a yield of 90%.

Mass: 468(M+), 439, 412, 397, 383, 355, 342, 327, 315, 301, 288, 273, 262, 249, 234, 221, 207, 192, 178, 165, 151, 137, 128, 115, 97, 81, 67, 55

(Step 3)

100 g (0.21 mol) of 4-(3,5-dibromo-phenyl)-4'-pentyl-bicyclohexyl-3-ene, 85.6 g (0.51 mol) of lithium bis(trimethylsilyl)amides, 3.0 g (0.011 mol) of tricyclo-hexylphosphine and 6.1 g (0.011 mol) of bis(dibenzylideneacetone)palladium were added, followed by the addition of 400 ml of toluene. The reaction vessel was kept at 90° C. under nitrogen atmosphere and the reaction was carried out for 12 hours. The progress of reaction was checked by GC/Mass. About 200 ml of ether was added to the reaction mixture to dilute it and about 300 ml of 1N hydrochloric acid was added to complete the reaction. The organic layer and water layer were washed using 1N sodium hydroxide and ether and extracted and then, the thus obtained organic layer was dried by addition of $MgSO_4$ and filtered. The solvent was removed by distillation under a reduced pressure and the thus obtained mixture was re-crystallized with methylene chloride, affording 39.0 g (0.115 mol) of a white solid with a yield of 54%.

Mass: 340(M+), 325, 312, 283, 269, 227, 214, 207, 200, 187, 173, 159, 145, 135, 122, 109, 99, 91, 81, 67, 55

(Step 4)

After 39 g (0.115 mol) of 5-(4'-pentyl-bicyclohexyl-3-en-4-yl)-benzene-1,3-diamine was dissolved in benzene and ethanol, 1.95 g of palladium(10 wt % on activated carbon) was added thereto and stirred under the pressure of 4 kg/cm$^2$ for 5 hours. After the completion of the reaction was checked, the reaction solution was filtered through cellite and the solvent was distilled under a reduced pressure, providing a light brown solid. The solid was re-crystallized with EA and ethanol, affording 16 g (0.047 mol) of trans isomer, 5-(trans-4-pentylbicyclohexyl-4-yl)-benzene-1,3-diamine with a yield of 40%.

Mass: 342(M+), 327, 313, 299, 285, 271, 260, 229, 216, 202, 189, 173, 163, 149, 142, 135, 122, 109, 100, 93, 81, 67, 55

$^1$H NMR (CDCl$_3$): 6.00 (s, 2H) 5.86 (s, 1H) 3.50 (s, broad, 4H) 2.25 (t, 1H) 1.80 (m, 4H) 1.5~1.0 (m, 23H) 0.90 (m, 3H)

Example 2

17.1 g (0.05 mol) of 5-(trans-4-pentylbicyclohexyl-4-yl)-benzene-1,3-diamine and 20.0 g (0.1 mol) of 4,4'-diaminodiphenylether (ODA) were dissolved in 237.4 g of N-methyl-2-pyrrolidone and this reaction solution was kept at 5° C., to which a reaction solution prepared by dissolving 48.3 g (0.15 mol) of 3,3',4,4'-benzophenonetetracarboxylic acid dianhydride (BTDA) in 237.4 g of N-methyl-2-pyrrolidone was slowly dropwise added for 2 hours and reaction was carried out for 4 hours. The reaction solution was precipitated in excessive amount of deionized water, providing polyamic acid. The polyamic acid solid was washed several times with deionized water. Thereafter, it was dried in a vacuum oven of 50° C. for two days, affording polyamic acid solids, and the properties of the obtained polymers are shown in Table 1 below.

Example 3

With the exception that 4,4'-diaminodiphenylether used in Example 2 was replaced by 4,4'-methylenebis(cyclohexylamine) (PACM), the same procedures as Example 2 were carried out, affording polyamic acid solids, and the properties of the obtained polymers are shown in Table 1 below.

Example 4

With the exception that 3,3',4,4'-benzophenonetetracarboxylic acid, dianhydride (BTDA) used in Example 2 was replaced by cis-1,2,3,4-cyclopentanetetracarboxylic acid, dianhydride (CPDA), the same procedures as Example 2 were carried out, affording polyamic acid solids, and the properties of the obtained polymers are shown in Table 1 below.

Example 5

With the exception that 3,3',4,4'-benzophenonetetracarboxylic acid dianhydride (BTDA) used in Example 2 was replaced by cis-1,2,3,4-cyclopentanetetracarboxylic acid dianhydride (CPDA) and 4,4'-diaminodiphenylether was replaced by 4,4'-methylenebis(cyclohexylamine) (PACM), the same procedures as Example 2 were carried out to, affording polyamic acid solids, and the properties of the obtained polymers are shown in Table 1 below.

Comparative Example 1

With the exception that alicyclic side-chained diamine used in Example 2 was replaced by 4'-(4-pentylcyclohexyl) biphenyl-3,5-diamine, the same procedures as Example 2 were carried out, affording polyamic acid solids, and the properties of the obtained polymers are shown in Table 1 below.

TABLE 1

Table 1. Properties of Obtained Polyamic Acid Derivatives

| | Number Average Molecular Weight (Mn) | Weight Average Molecular Weight (Mw) | Polydisperse Index (Mw/Mn) | Cut-off Wavelength in UV-vis region (nm) |
|---|---|---|---|---|
| Ex. 2 | 20600 | 34300 | 1.7 | 304 |
| Ex. 3 | 16900 | 39900 | 2.4 | 297 |
| Ex. 4 | 2400 | 3200 | 1.4 | 277 |
| Ex. 5 | 2000 | 8300 | 4.1 | 261 |
| Com. Ex. 1 | 16900 | 26700 | 1.6 | 314 |

As seen in Table 1 above, the polyamic acid derivatives of Examples 2 to 5 according to the present invention showed improved permeability when compared with that of Comparative Example 1, and they had the weight average molecular weight of 3200 to 40000 g/mol and the polydisperse index of 1.4 to 4.1 and thus they were suitable as materials for alignment films.

Also, the polyamic acid solids prepared in Examples 4 to 5 and Comparative Example 1 were dissolved in a solution of NMP and 2-butoxyethanol which were mixed in a ratio of 4:1 by volume, in an amount of 4% by weight. The thus obtained solution was filtered through a filter of 0.1 um and coated onto a glass substrate with clear conductive films being patterned thereon by a spinner method in a thickness of 600 Angstrong. After coating, it was pre-calcined at 90° C. for 3 min and calcined at 210° C. for 1 hour, and the characteristics of the thus obtained thin film were evaluated and summarized in Table 2 below.

TABLE 2

Table 2. Properties of Polyimide Derivatives Prepared After Heat Curing

| | Surface Tension (dyn/cm) | Solubility | | | | | |
|---|---|---|---|---|---|---|---|
| | | Water | Chloroform | IPA | Acetone | THF | DMAC | NMP |
| Ex. 5 | 32.3 | − | + | − | ++ | ++ | ++ | ++ |
| Ex. 4 | 32.2 | − | + | + | + | ++ | + | ++ |
| Com. Ex. 1 | 37.4 | − | − | − | − | − | − | − |

As seen in Table 2, the polyimide films of Examples 4 to 5 showed the surface tension of 32.2 to 32.3 and in particular, their solubility in several organic solvents showed great improvement when compared with that of Comparative Example 1.

Further, two substrates on which liquid crystal alignment films were formed as above were counter-arranged with a certain space (cell gap) without rubbing the alignment film sides, the surroundings of the two substrate were joined using a sealant, the cell gap defined by the substrate surface and sealant was filled with liquid crystal by injection, and the injection hole was sealed whereby liquid crystal cells were manufactured. The characteristics of the thus produced liquid crystal cells are shown in Table 3 below.

TABLE 3

Table 3. Characteristics of Liquid Crystal Cells

|  | Alignment Properties | Pretilt Angle (Degree) | Voltage-Holding Ratio (%) |
|---|---|---|---|
| Ex. 2 | Good | 89 | 90 |
| Ex. 3 | Good | 90 | 90 |
| Ex. 4 | Good | 89 | 93 |
| Ex. 5 | Good | 90 | 89 |
| Com. Ex. 1 | Good | 90 | 87 |

As seen in Table 3 above, Examples 2 to 5 according to the present invention showed excellent vertical alignment by non-rubbing methods and their voltage-holding ratios were remarkably excellent when compared with Comparative Example 1.

The above-identified properties were evaluated using the following methods.

1) Weight Average Molecular Weight of Polymers

To calculate the weight average molecular weights of the polymers, gel permeation chromatography (GPC) was measured. Retention time of columns where polymer substances were filled using dimethylacetamide (DMAc) as a mobile phase at 60° C. was measured, and the average molecular weight of the polyamic acid solid was calculated by the adjustment of the retention time and the average molecular weight of stylene polymer. It is advisable for polymers constituting liquid crystal alignment materials to have the weight average molecular weight of 2,000 to 1,500,000 g/mol or so.

2) UV-Vis Permeability of Liquid Crystal Alignment Film

Liquid cells were filled with the polyamic acid solution, of which permeability graph in UV-vis regions was obtained using a UV-vis spectrometer. Cut-off wavelengths were calculated from the graph of permeability.

3) Surface Tension

It was obtained from the relationship between surface free energy (surface tension) of liquid crystal alignment films and contact angles from the contact angle of iodized methylene and the contact angle of pure water which were measured over liquid crystal alignment films in accordance with the methods described in the document (D. K. Owens. J. Appl., Pol., Sci. vol 13. 1741-1747 (1969)). The contact angles were measured using KRSS DSA100 and obtained by adding water and iodized methylene over the films and calculating the average value of the contact angles for 10 sec.

4) Solubility of Liquid Crystal Alignment Films

After the polyimide alignment films were formed on glass substrates by a spinner method, it was quenched in each organic solvent at a room temperature for 30 sec and the solubility of the alignment films was measured. Each alignment film was calcined under the conditions of temperature at which imidization was 100% completed. They are designated as follows: no change on coated alignment film as '−', slight chip-off of surface as '+', and complete chip-off as '++'.

5) Pretilt Angle of Liquid Crystal Display Device

It was measured by a crystal rotation method using a He—Ne laser light in accordance with the methods described in the document (T. J. Schffer, et. al., J., Appl., Phys., vol. 19, 2013 (1980)).

6) Alignment Properties of Liquid Crystal

When voltage was applied to liquid crystal display devices in on/off mode, the presence/absence of abnormal domains among the liquid crystal cells was observed with a microscope, and when there was no abnormal domain, it was designated 'good'.

7) Voltage-Holding Ratio of Liquid Crystal Display Device

After the voltage of 5 V is applied to liquid crystal display devices for 60 microseconds, voltage-holding ratio was measured after 16.67 milliseconds from the removal of application.

INDUSTRIAL APPLICABILITY

As described in the above, the side-chained diamine compounds of formula 1 of the present invention are useful for the manufacturing of polyimide resins for non-rubbing vertical alignment materials, and the polyimide resins prepared using the diamine compounds have good vertical alignment of liquid crystal and can exert pretilt angles of 89 degree or more with non-rubbing methods regardless of rubbing process conditions and furthermore, the polyimide resins in accordance with the invention have remarkably improved clarity and solubility against organic solvents and thus they are useful as alignment material for liquid crystal display device.

The invention claimed is:

1. A method for the preparation of the diamine compound represented by formula 1:

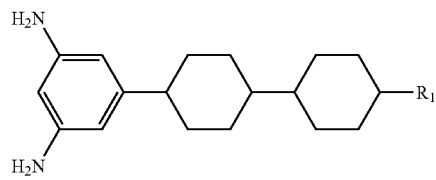

wherein $R_1$ is an alkyl group having 5 to 7 carbon atoms or alkoxy group having 5 to 7 carbon atoms, comprising:

a) preparing a compound of formula 2 by reacting 4'-alkylbicyclohexyl-4-one compound with 1,3,5-tribromobenzene:

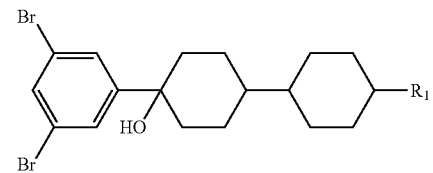

wherein $R_1$ is an alkyl group having 5 to 7 carbon atoms or alkoxy group having 5 to 7 carbon atoms;

b) preparing a compound of formula 3 by reacting the compound of formula 2 with p-toluenesulfonic acid 1-hydrate:

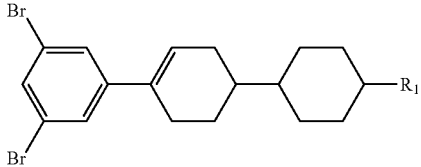

wherein $R_1$ is an alkyl group having 5 to 7 carbon atoms or alkoxy group having 5 to 7 carbon atoms;

c) preparing a compound of formula 4 by reacting the compound of formula 3 with lithium bis(trimethylsilyl) amide, (dibenzylideneacetone)palladium, and tricyclohexylphosphine in combination:

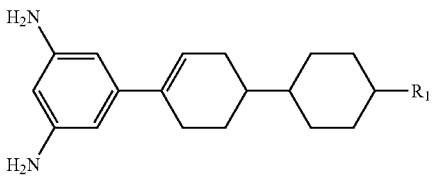

wherein $R_1$ is an alkyl group having 5 to 7 carbon atoms or alkoxy group having 5 to 7 carbon atoms; and d) performing the addition of hydrogen to the compound of formula 4 under a Pd/C catalyst and separating a trans isomer compound therefrom.

* * * * *